United States Patent
Soto

(10) Patent No.: US 9,248,481 B1
(45) Date of Patent: Feb. 2, 2016

(54) SEALED WASTE DISPOSAL MINIMIZING AIRBORN PARTICLE EXPOSURE

(71) Applicant: Louis M. Soto, Miramar, FL (US)

(72) Inventor: Louis M. Soto, Miramar, FL (US)

(*) Notice: Subject to any disclaimer, the term of this patent is extended or adjusted under 35 U.S.C. 154(b) by 573 days.

(21) Appl. No.: 13/685,135

(22) Filed: Nov. 26, 2012

Related U.S. Application Data

(63) Continuation-in-part of application No. 11/946,283, filed on Nov. 28, 2007, now Pat. No. 7,854,107, and a continuation-in-part of application No. 12/788,002, filed on May 26, 2010, now Pat. No. 8,316,625.

(51) Int. Cl.
*B65B 31/02* (2006.01)
*A61L 9/20* (2006.01)
(Continued)

(52) U.S. Cl.
CPC ... *B09B 5/00* (2013.01); *A61L 9/16* (2013.01); *A61L 9/20* (2013.01); *A61L 9/205* (2013.01); *A61L 9/22* (2013.01); *A61L 11/00* (2013.01); *B08B 15/02* (2013.01); *B08B 15/026* (2013.01); *B09B 3/0075* (2013.01); *B25J 21/02* (2013.01); *B65B 31/02* (2013.01); *B65F 7/00* (2013.01);
(Continued)

(58) Field of Classification Search
CPC .............. A61L 11/00; A61L 9/16; A61L 9/20; A61L 9/205; A61L 9/22; A61L 2209/11; B25J 21/02; B09B 3/0075; B09B 3/0066; B65B 31/00; B65B 31/02; B65B 31/024; B65F 2210/188; B08B 15/02; B08B 15/026
USPC .......... 53/493, 502, 77, 507, 510, 512, 284.7; 110/235, 242, 346; 312/1; 422/4, 24; 588/249.5, 260, 900
IPC .................................. B65B 31/02,29/00, 25/00
See application file for complete search history.

(56) References Cited

U.S. PATENT DOCUMENTS 3,511,022 A * 5/1970 Finley et al. ..................... 53/512
3,596,429 A * 8/1971 Vogt ................................... 53/67
(Continued)

FOREIGN PATENT DOCUMENTS

EP     600808 A1 *  6/1994  ................. 110/235
FR    2758540 A1    7/1998
(Continued)

OTHER PUBLICATIONS

EPO machine translation of FR 2758540, retrieved Jun. 9, 2015, espacenet.com, 7 pages.*
(Continued)

*Primary Examiner* — Stephen F Gerrity
(74) *Attorney, Agent, or Firm* — Patents on Demand P.A.; Brian K. Buchheit; Scott M. Garrett

(57) ABSTRACT

A disposal unit can include a substantially air tight chamber, an insertion component for inserting waste into the chamber, a disposal container for removing the inserted waste from the disposal unit, a container sealant mechanism configured to allow a sealing of the disposal container, and an air extraction unit. The air extraction unit captures air or airborne particles from the substantially air tight chamber to minimize exposure to the air or the airborne particles from the inserted waste. The exposure to the air or airborne particles is minimized to humans placing the waste into the insertion component, to humans removing the disposal container from the disposal unit, or to humans proximate to the disposal unit.

19 Claims, 9 Drawing Sheets

(51) Int. Cl.

| | | |
|---|---|---|
| *B09B 5/00* | (2006.01) | |
| *B25J 21/02* | (2006.01) | |
| *B08B 15/02* | (2006.01) | |
| *A61L 9/16* | (2006.01) | |
| *A61L 11/00* | (2006.01) | |
| *B09B 3/00* | (2006.01) | |
| *A61L 9/22* | (2006.01) | |
| *B65F 7/00* | (2006.01) | |

(52) U.S. Cl.
CPC ........ *A61L 2209/11* (2013.01); *B65F 2210/188* (2013.01)

(56) References Cited

U.S. PATENT DOCUMENTS

| | | | | |
|---|---|---|---|---|
| 3,939,998 | A * | 2/1976 | Soltermann | 414/404 |
| 4,297,827 | A * | 11/1981 | Allison | 53/282 |
| 4,592,192 | A * | 6/1986 | Jacob et al. | 53/512 |
| 4,688,371 | A * | 8/1987 | Hecht | 53/502 |
| 4,979,967 | A * | 12/1990 | Walter et al. | 95/214 |
| 4,991,633 | A * | 2/1991 | Wong | 141/5 |
| 5,005,496 | A | 4/1991 | Nagata | |
| 5,007,232 | A * | 4/1991 | Caudill | 53/426 |
| 5,027,578 | A * | 7/1991 | Natterer et al. | 53/86 |
| 5,054,696 | A | 10/1991 | Mennel | |
| 5,178,828 | A * | 1/1993 | Uesugi | 422/22 |
| 5,185,126 | A * | 2/1993 | Adamski et al. | 422/38 |
| 5,425,316 | A * | 6/1995 | Malone | 110/190 |
| 5,511,594 | A * | 4/1996 | Brennan et al. | 141/98 |
| 5,528,880 | A * | 6/1996 | Landolt | 53/432 |
| 5,715,646 | A * | 2/1998 | Smekens | 53/121 |
| 5,791,123 | A * | 8/1998 | Bolz | 53/434 |
| 5,806,282 | A * | 9/1998 | Hansen | 53/432 |
| 5,810,060 | A * | 9/1998 | Bolz et al. | 141/97 |
| 5,881,535 | A * | 3/1999 | Gliniecki et al. | 53/410 |
| 5,890,781 | A * | 4/1999 | Ryder | 312/1 |
| 5,972,291 | A * | 10/1999 | Healy et al. | 422/22 |
| 6,367,518 | B2 | 4/2002 | Duncan | |
| 6,428,122 | B1 * | 8/2002 | Henry et al. | 312/1 |
| 6,581,647 | B1 * | 6/2003 | Leidlein et al. | 141/2 |
| 6,742,703 | B2 | 6/2004 | Esakov et al. | |
| 6,997,313 | B2 | 2/2006 | Rigling | |
| 7,017,306 | B2 | 3/2006 | Ryder | |
| 7,114,629 | B2 | 10/2006 | Panek, Jr. | |
| 7,174,602 | B1 | 2/2007 | Foral | |
| 2001/0004182 | A1 * | 6/2001 | Bennison | 312/1 |
| 2003/0038564 | A1 | 2/2003 | Drinkwater | |
| 2005/0004537 | A1 * | 1/2005 | Dunn et al. | 604/322 |
| 2006/0119232 | A1 | 6/2006 | Tattershall | |
| 2009/0149689 | A1 * | 6/2009 | Crawford et al. | 588/3 |
| 2009/0280027 | A1 * | 11/2009 | Hayman, Jr. | 422/4 |

FOREIGN PATENT DOCUMENTS

| | | | | |
|---|---|---|---|---|
| FR | 2862953 A1 * | 6/2005 | | B65B 31/02 |
| JP | 52-144600 A | 12/1977 | | |
| JP | 63080115 A * | 4/1988 | | 110/235 |
| JP | 03-275422 A | 12/1991 | | |
| JP | 05185058 A * | 7/1993 | | 110/235 |
| JP | 05185060 A * | 7/1993 | | 110/235 |
| JP | 05237469 A * | 9/1993 | | 110/235 |
| WO | 2004110867 A1 | 12/2004 | | |

OTHER PUBLICATIONS

"Preventing Occupational Exposure to Antineoplastics and Other Hazardous Drugs in Workplace Settings,"NIOSH, Pub. No. 2004-165, Sep. 2004, 48 pages.

Spivey, S.M., et al., "Determining Sources of Workplace Contamination with Antineoplastic Drugs and Comparing Conventional IV Preparation With a Closed System," Hospital Pharmacy, 38(2):135-139, dated 2003, 1 page.

"ASHP Guidelines on Handling Hazardous Drugs," Am. J. Health-System Pharm., 2006-63, 1172-93, 20 pages, numbered 34-53.

Connor, T., "NIOSH Study of Health Care Workers in Three Sites-:Study Design and Results," 44th ASHP Midyear Clinical Meeting & Exhibition, Dec. 6-10, 2009. 48 pages.

* cited by examiner

SEALED WASTE DISPOSAL MINIMIZING AIRBORN PARTICLE EXPOSURE

CROSS-REFERENCE TO RELATED APPLICATIONS

This application is a continuation-in-part of U.S. patent application Ser. No. 12/788,0002, filed 26 May 2010, now U.S. Pat. No. 8,316,625, which is a continuation-in-part of U.S. patent application Ser. No. 11/946,283, filed 28 Nov. 2007, now U.S. Pat. No. 7,854,107, The entire contents of U.S. application Ser. No. 11/946,283 and Ser. No. 12/788,002 are incorporated by reference herein.

BACKGROUND

The present invention relates to the field waste disposal and, more particularly, to sealed waste disposal minimizing airborne particle exposure.

The majority of trash receptacles include a lid, which is able to be opened, permitting waste to be placed inside. An interior bag of the trash receptacle is often able to be "tied" or otherwise manually sealed. Many types of refuse, however, can pose exposure hazards, which current trash disposal technologies fail to address. The hazards can result from airborne substances (which include vapors and air medium) being emitted from waste during the disposal process.

This can be true, for example, in a medical context, where bed sheets, gowns, linens, drinking cups, and other material are disposed of, each of which can contain traces of blood, sweat, and other body fluids, which can be hazardous to others. For instance, chemotherapy patients are occasionally irradiated, which results in their fluids containing traces of radioactivity to which waste disposal personnel at hospitals are constantly exposed. Additionally, airborne pathogens can be especially problematic for waste disposal employees at hospitals, who have a much higher than normal rate of health problems caused by constant exposure to hazardous material.

Other contexts where waste disposal practices are currently insufficient and/or dangerous include research lab waste disposal situations, toxic spill situations, generic hazmat situations, biological/chemical attacks in a terrorism/military situation, outbreak and epidemic situations, flooding and other national emergencies where mold, fungus, bacteria, viruses, and other potentially harmful substances are to be expected.

Public concern over the proper treatment and disposal of chemical waste products has increased over the past several years. This increase is due in part to an increased public awareness of dangerous chemicals being exposed to the environment that can have deleterious effects when improperly disposed of from within hospitals, out-patient clinics, and physicians' offices. Despite this increased awareness within limited contexts, few effective measures are being taken to resolve underlying problems. For example, hospitals currently have established awareness programs designed to teach its personnel to handle potentially harmful materials with care. These programs are designed to appease public pressure, but not to address the fundamental problem that current waste disposal techniques pose a health risk regardless of a level of care taken. What is needed is a new type of waste disposal receptacle, which minimizes (or eliminates) human contact with toxic wastes, which includes protection from airborne vapors.

BRIEF DESCRIPTION OF THE DRAWINGS

There are shown in the drawings, embodiments which are presently preferred, it being understood, however, that the invention is not limited to the precise arrangements and instrumentalities shown.

DETAILED DESCRIPTION

Figure 1:
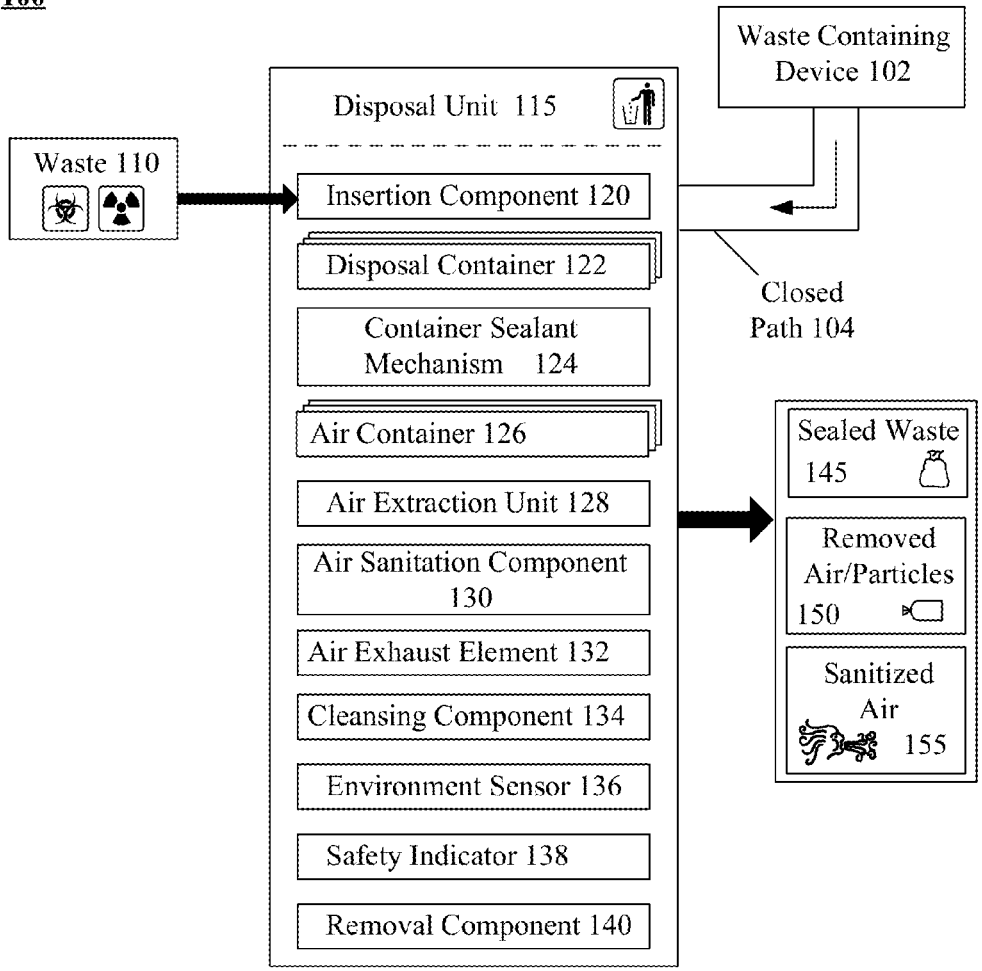
FIG. 1 is a schematic diagram of a waste disposal system for safely disposing hazardous material in accordance with an embodiment of the inventive arrangements disclosed herein.

The present invention provides a solution for safely disposing potentially hazardous materials in accordance with an embodiment of the inventive arrangements disclosed herein. The solution reflects an environmentally closed disposal container, which includes one or more sealable bags. Waste can be placed within the closed disposal container, where the waste fills a current opening of one of the sealable bags without exposing a handler to airborne emissions. Once placed in the container, the open bag can be sealed, without compromising the environmentally closed system. For example, sealed gloves can extend into the sealed container, which permit the handler to close and seal the open bag. Once the bag is closed and/or sealed, a pump can remove/filter the air from within the closed disposal container. In one embodiment, a bladder can be expanded to contain the air removed from the disposal container. An optional indicator can engage to alert the handler when the disposal system is "safe," at which point the sealed bag can be safely removed without harm to the handler. A unique feature of the claimed disposal system is that it is able to safely capture any and all volatile gases and airborne particles that may under traditional conditions emanate from the waste to harm a handler.

The present invention can be implemented in accordance with numerous aspects consistent with the materials presented herein. One aspect of the present invention can include a waste disposal unit comprising an approximately air tight chamber which is sufficiently air tight to ensure that harmful airborne byproducts of waste do not escape into an environment external to the waste disposal unit. Depending upon a type of waste being handled, a perfect air-tight seal is not needed, but a seal sufficient to prevent harm to a unit operator is acceptable. The unit can include an insertion component for inserting waste into the approximately air tight chamber. A distinct air tight region of the air tight chamber can contain a disposal container within which waste received via the insertion component is able to be placed. Another distinct region of the approximately air tight chamber can be an air holding region distinct from the air tight region and a remaining region of the approximately air tight chamber. The unit can include an air extraction unit configured to capture air from the remaining region and to place the captured air in the air holding region. The air extraction unit can further convey the captured air from the air holding region and place it within the air tight region (e.g., the disposal container). A manipulator for sealing the disposal container after the air extraction unit has conveyed air into it from the air holding region can also be part of the system. Once the disposal container has been sealed, the sealed container can be removed from the unit via a removal component.

Another aspect of the present invention can include a closed system for disposing of waste having potentially harmful airborne emissions. The closed system can include a sealable disposal chamber, an insertion tube, a set of tubing, an air pump, a manipulator, a removal component, and a set of user controls. The sealable disposal chamber can be configured to prevent an escape of the potentially harmful airborne emissions. The insertion tube can be used for inserting wastes and can include a one-way seal. The insertion tube can also include an opening for attaching an air tight waste disposal bag. When the air tight waste disposal bag is connected to the opening, the bag can form an air tight boundary between itself and a remainder of the sealable disposable chamber. The tubing can have sealable openings into the remainder of the sealable disposal chamber, into the insertion tube, and into an air holding region. The air pump can be connected to the set of tubing. One user control can activate the pump to convey air from the remainder of the sealable disposal chamber into the air holding region. Another user control can activate the pump to convey air from the air holding region to the sealable disposal chamber. The manipulator can permit a sealing of the sealable disposal container while the sealable disposal unit is sealed. The removal component can permit sealed ones of the disposal containers to be safely removed from the closed system.

Still another aspect of the present invention can include a method for disposing waste. The method can include a step for receiving waste through an aperture of a disposal unit having a substantially closed environment. The received waste can be placed within an air tight disposal container. An opening of the disposal container can be sealed to separate the disposal container from a remainder of the substantially closed environment. Air included in the remainder of the substantially closed environment can be captured and placed in a holding unit. The captured air can be ejected from the holding unit into the air tight disposal container. The disposal container containing the received waste and the ejected air can be sealed. The disposal unit can be thereafter opened so that the sealed disposal container is able to be discarded.

It should be noted that various aspects of the invention can be implemented as a program for controlling computing equipment to implement the functions described herein, or as a program for enabling computing equipment to perform processes corresponding to the steps disclosed herein. This program may be provided by storing the program in a magnetic disk, an optical disk, a semiconductor memory or any other recording medium. The program can also be provided as a digitally encoded signal conveyed via a carrier wave. The described program can be a single program or can be implemented as multiple subprograms, each of which interact within a single computing device or interact in a distributed fashion across a network space.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in one or more any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, or device. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, or a magnetic storage device.

The computer-readable medium can be a non-transitory storage medium in which data is retained in a digitally encoded form. The computer-readable medium can be a physical, tangible storage medium able to retain information, which is extractable by computing equipment to obtain the data content that was stored upon the storage medium.

Computer program code for carrying out operations of the present invention may be written in any combination of one or more programming languages, including an object oriented programming language such as JAVA, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

FIG. 1 is a schematic diagram of a waste disposal system 100 for safely disposing hazardous material in accordance with an embodiment of the inventive arrangements disclosed herein. As shown, waste 110 can be placed within a disposal unit 115 through an insertion component 120. In one embodiment, a closed path 104 can exist between an external waste containing device 102 and the disposal unit 120 to minimize handler contact/exposure with the waste 110. The closed path 104 can include numerous directional components, specifics of which vary based upon a type of waste 110 being moved from device 102 to unit 115. For example, when the waste 110 consists of airborne particles, powders, etc., the closed path 104 can include a directional ventilation system for directing air/small particles. When the waste 110 is liquid, the closed path 104 can include plumbing. When the waste 110 is solid, the path 104 can include a conveyor belt or other mechanical conveyance mechanisms, such as a gravity based disposal shoot terminating in the unit 115. When waste 110 is unknown or non-uniform, suitable combinations of path 104 components can be utilized to handle any type of waste 110.

That is, the disposal unit 115 can be a substantially closed system, designed to permit complete waste 110 containment. For example, when the waste 110 can include airborne particles, the unit 115 can be a closed, air-tight system designed to prevent an escape of airborne particles. The insertion component 120 can ensure the waste 110 is sealed once placed in unit 115 to prevent external leakages and exposure. Disposal unit 115 can be implemented as any of a variety of different disposal containers 122, each able to contain waste 110, which can be sealed by the container sealant mechanism 124 to prevent the waste 110 from escaping once contained. For example, the containers 122 can include bags, hardened plastic baskets, chemo bins, and the like. Waste disposed of in the containers 122 (which is prevented from escaping) can include vapors, radiation, and small particles.

The container sealant mechanism 124 can represent one or more mechanisms for sealing the disposal container 122. Contemplated examples of the container sealant mechanism 124 can include, but are not limited to, one or more manual manipulators, an automated vacuum-sealing component, an automated heat-sealing component, use of an adhesive to seal container 122, and the like. The seal established by the container sealant mechanism 124 can be an air tight one.

Once the disposal container 122 is sealed, an air extraction unit 128 can remove airborne particles or other potentially dangerous trace elements from the disposal unit 115. The removed air can be placed within an air container 126. In one embodiment, the air container 126 can be a separate container from disposal container 122. In another implementation, the disposal container 122 can be an air tight container that also functions as the air container 126. In still another implementation, the air container 126 can be a separately sealed container included inside the disposal container 122. Of course, using the disposal container 122 to contain air can alter an order in which the disposal container 122 is sealed relative to when the disposal unit 115 extracts the air.

After air collection and the sealing of the disposal container 122, the air collected in the air container 126 can be treated by an air sanitation component 130. The air sanitation component 130 can include one or more air treatment mechanisms configured to improve the air quality of the collected air to a predetermined/acceptable level.

Examples of air treatment mechanisms that can be utilized in the air sanitation component 130 can include, but are not limited to, a heat sterilization mechanism, an incineration mechanism, an ultraviolet (UV) disinfection mechanism, a filtration mechanism, a photo-catalytic sanitation mechanism, an oxidation mechanism, an ionization mechanism, and the like. For example, the air within the air container 126 can be exposed to a UV disinfection wand before passing through an active carbon filter. Any number (0 . . . N) of different sanitation components 130 can be cooperatively utilized.

Embodiments are contemplated, where air treatment resulting from use of one or more components 130 is sufficient to permit sanitized air to be conveyed from disposal unit 115 to an external environment, as opposed to requiring it be stored in air container 126. Further, embodiments are contemplated where sensors are used to examine air inside the unit 115, where different steps are taken based upon sensor results. For example, results can indicate that interior air of unit 115 should be cycled (0 . . . N times) through one or more of the sanitation components and then ejected into an exterior environment (by air extraction unit 128). Different results can indicate that interior air of unit 115 should be captured in air container 126, then further sanitation actions (using components 130 and/or cleaning component(s) 134) should be taken to additionally cleanse unit 115 of harmful vapors/residue.

Once the collected air has been sanitized to the predetermined level, an air exhaust element 132 can be used to expel the sanitized air 155 from the disposal unit 115. The air exhaust element 132 can be configured to optionally expel the sanitized air 155 into the immediate environment of the disposal unit 115. Alternately, the air exhaust element 132 can be connected to a ventilation system (not shown) external to the disposal unit 115.

The disposal unit 115 can optionally include an additional cleansing component 134, such as a component that sprays a sanitizing liquid into the interior of disposal unit 115 to ensure the disposal unit 115 is free of waste 110. Disposal unit 115 can also include one or more optional environment sensors 136 designed to detect when the disposal unit 115 is free from harmful waste 110 (which includes vapors). The environment sensor 136 can be linked to a removal component 140 so that the removal component 140 is unable to be opened until the interior environment of the disposal unit 115 is safe.

An optional safety indicator 138 can provide an indicator as to conditions determined by the one or more environment sensors 136. For example, the safety indicator 138 can display text concerning radiation levels, airborne pathogen levels, and other important metrics concerning the interior condition of the disposal unit 115. In another example, the safety indicator 138 can be implemented as a light providing a warning when it is safe/unsafe to open the disposal unit 115. The removal component 140 can be a component through which the sealed waste 145 and/or removed air/particles 150 are able to be safely removed.

System 100 can be configured/adapted for any situation involving 110 waste disposal. Some originally solid waste 110 is burned, compacted, rendered inert, or otherwise processed during the disposal process. Processing components can be added to unit 115 so that these disposal processes can be performed in a closed environment in a manner safe for a human handler or operator of unit 115.

It should be appreciated that the details for efficiently and economically implementing system 100 can vary according to a usage situation. One important feature to note of system 100 is its ability to establish a closed environment within container 122, where received waste 110 is converted into sealed waste 140 without exposing a handler to hazards of the waste 110. For instance, the unit 115 can capture any and all volatile gases, airborne particles, pathogens, biological hazards, chemicals, offensive smells, and the like within the closed environment.

In one configuration, system 100 can have hospital outpatient clinic, pharmacy, and physicians' office applications. In such applications, it can provide a safety feature by securely allowing the disposal of chemically tainted materials while simultaneously capturing volatile and noxious gases that may be construed as not being present. The system 100 can be configured to satisfy numerous regulations, such as those of United States Pharmacopeia (USP) 797. In contrast, pre-existing waste disposal systems fail to resolve issues of volatile gases and its effects on the environment. Conventionally utilized High Efficiency Particulate Air (HEPA) filters do not impede such volatile gases. Furthermore, use of conventional biological glove boxes do not sufficiently address aerosolized gases except to otherwise vent them into the environment to be further diluted with the air. Unlike other solutions, system 100 can allow hospital produced byproducts (e.g., chemotherapy byproducts and residual volatile gases, for example) to be collected, captured, and then incinerated. Thus eventually rendering the materials innocuous to the surrounding environment.

It should be appreciated that system 100 is not limited to health care applications. In one contemplated configuration, system 100 can be adapted for household use, preventing smells from coming out of garbage bags. System 100 can also be adapted for commercial food industries such as for kitchens of ships, aircrafts, cruise liners, tour buses, restaurants, and trains. A further application for system 100 is for handling industrial waste, such as wastes produced by chemical refineries, industrial cleaner containment, manufacturing byproducts, and the like. Moreover, system 100 can be used for disaster cleanup, such as for flood cleanup, hurricane cleanup, and the like, where often unknown and potentially hazardous materials must be discarded in volume.

Subsequent figures of the application provide a complete embodiment for a waste disposal unit, where solid wastes are generated, which have potentially hazardous airborne components. Consequently, the containment unit/system of this embodiment is designed to dispose of waste in a closed environment, to seal a container containing waste, and to clear the air within the closed environment before permitting the disposal environment to be opened for removal of the sealed waste. The specifics provided for this embodiment are to illustrate a concept only and the invention is not to be limited to the detailed specifics.

For example, the specifics show a containment unit where gloves are used as manipulators. Derivative embodiments where other manipulators, such as mechanical manipulators and/or robotic arms are contemplated. In another example, an insertion component for receiving waste is shown as a tube, which in other contemplated embodiments can be implemented as a revolving door in which a seal is maintained, a sliding aperture, and the like. Further, the containment unit shown in one or more of the drawings indicates a square, but other shapes, can be utilized and may be better suited depending upon application. Any adaptation to details of the system 100 are contemplated, including known adaptations for specially handling of specific types of wastes 110, such as flammable wastes, corrosive wastes, biological wastes, radioactive wastes, and the like.

Figure 2:
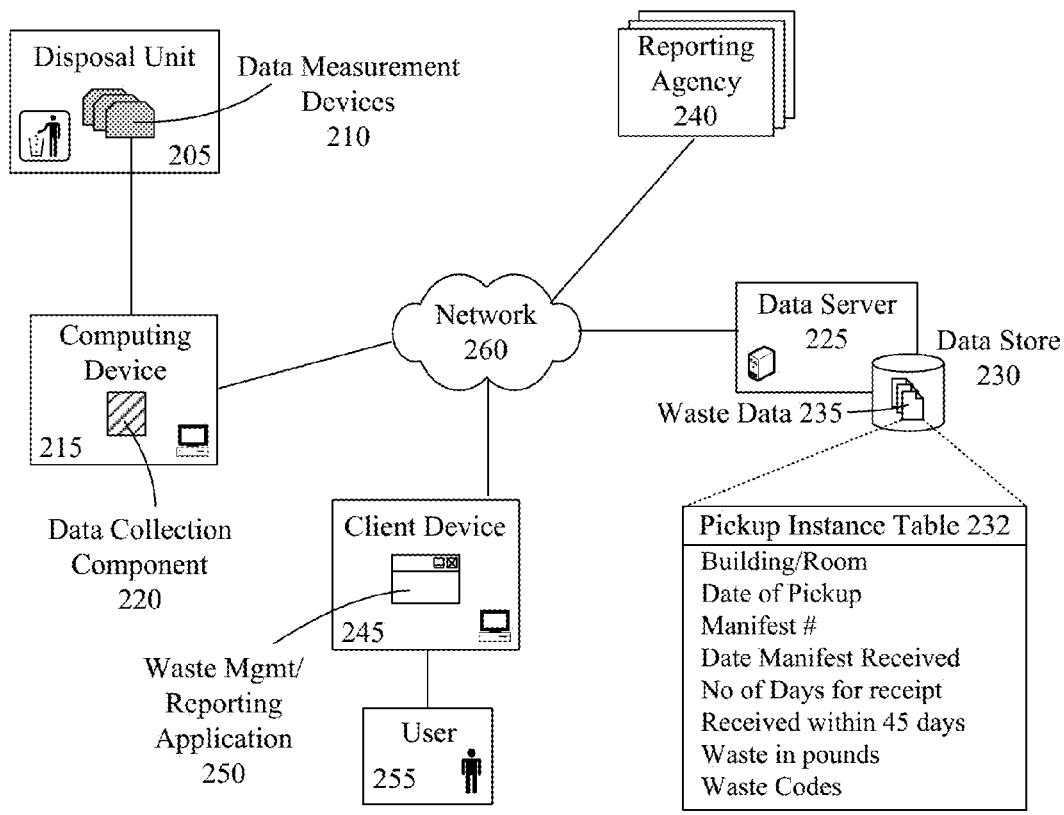
FIG. 2 is a schematic diagram of a waste disposal system that collects waste data regarding hazardous wastes processed by a disposal unit in accordance with an embodiment of the inventive arrangements disclosed herein.

FIG. 2 is a schematic diagram of a waste disposal system 200 that collects waste data 235 regarding the hazardous wastes processed by a disposal unit 205 in accordance with an embodiment of the inventive arrangements disclosed herein. In system 200, data measurements devices 210 installed within the disposal unit 205 can automatically collect one or more elements of waste data 235 that can be conveyed over a network 260 to a data server 225 for storage.

The disposal unit 205 can represent one of the many possible configurations described within U.S. patent application Ser. No. 11/946,283, which is to be considered as having been incorporated herein in its entirety.

For instance, and in one embodiment, the disposal unit 205 can be a disposal unit for a compounding aseptic containment isolator to prevent vapors and other wastes and/or waste byproducts from escaping. In another example, the disposal unit 205 can be coupled to a class II or type 2B biological safety cabinet. The disposal unit 205 is not limited to these configurations, which are provided for illustrative purposes only.

The disposal unit 205 can be designed to conform to state and/or federal regulation related to waste disposal and handling, especially hazardous wastes. For example, the disposal unit 205 and processes detailed herein can conform to the Resource Conservation and Recovery Act (RCRA) or 40 CFR Section 260. Thus, disposal unit 205 can be suited handling wastes falling under any of the four hazardous waste lists established by Environmental Protection Agency (EPA) regulations. This includes F-lists (non-specific source wastes), K-list (source-specific wastes), P-list, and U-list (discarded commercial chemical products). In one embodiment, special emphasis can be placed on using disposal unit to handle discarded chemical products (currently defined by 40 CFR Section 261.33). Additionally, the disposal unit 205 can handle characteristic wastes that exhibit one or more of the four characteristics (Ignitability, Corrosively, Reactivity, and Toxicity) defined in 40 CFR Part 261, Subpart C. Any of the definitions for hazardous wastes and the requirements for handling of such found in the RCRA are to be considered within scope of the disclosure, and are able to be referenced and applied herein.

In one embodiment, wastes handled by the disposal unit 205 can include waste pharmaceuticals. Currently there are approximately 31 commercial chemical products listed on RCRA's P- and U-lists that have pharmaceutical uses. As the P- and U-lists are based on chemical designations, this number does not completely represent the total number of brand name pharmaceuticals that may actually be listed hazardous wastes. For example, the following chemotherapy drugs, CTX, Cytotoxan, Neosar and Procytox, are U058 (cyclophosamide).

In addition, waste pharmaceuticals may also be hazardous because they exhibit one or more of the four characteristics of hazardous waste: ignitability, corrosivity, reactivity and toxicity. Characteristic pharmaceutical wastes include those that exhibit the ignitability characteristic, such as solutions containing more than 24% alcohol. An example of a pharmaceutical that may exhibit the reactivity characteristic is nitroglycerine. Pharmaceuticals exhibiting the corrosivity characteristic are generally limited to compounding chemicals, including strong acids, such as glacial acetic acid, and strong bases, such as sodium hydroxide. Depending on the concentration in different pharmaceutical preparations, pharmaceuticals may also exhibit the toxicity characteristic because of the use of arsenic (D004), barium (D005), cadmium (D006), chloroform (D022), chromium (D007), lindane (D013), m-cresol (D024), mercury (D009), selenium (D010), and silver (D011). As thousands of over-the-counter or prescription drugs are currently approved for sale in the U.S., it is difficult to provide a precise number of pharmaceuticals that are listed and/or characteristic under RCRA.

The disposal unit 205 can also be adapted to handle non-hazardous wastes (e.g., waste regulated by 40 CFR Parts 239 through 259).

Additional federal regulations (not RCRA defined), such as those established by EPS, DOT, and OSHA can define rules, standards, and requirements for handling hazardous and non-hazardous wastes, which disposal unit 205 can conform to, and measurement devices 210 can assist with the compliance monitoring of.

Various state and county laws can also be utilized when defining hazardous wastes that disposal unit 205 is designed to handle in accordance with applicable regulations. For example, the Florida Administrative Code (FAC) rule chapters 62-730 define and govern hazardous wastes in Florida. Every state (and even some counties and local regulations) establish waste disposal regulations, which the disposal unit 205 and data measurement devices 210 can be adapted to handle (and to automatically monitor and report).

The reporting agencies 240 used herein can include federal, state, and local reporting agencies as well as corporate defined ones (that may not be subject to a state, federal, or local regulation.). Thus reporting agencies 240 can include, but are not limited to, the EPA, DOT, CBOX, OSHA, and state specific agencies.

Turning back to FIG. 2, the disposal unit 205 has been modified (from the cross referenced case) to contain one or more data measurements devices 210. The data measurements devices 210 can correspond to a variety of equipment designed to measure one or more relevant properties of the waste being processed by the disposal unit 205, the byproducts produced by the processing of the waste, and/or the disposal unit 205 itself. The relevant properties of waste captured by the measurement devices 210 can include those defined by federal (e.g., 40 CFR Section 260), state (e.g., FAC rules 62-730), local, or company established regulations. Thus, the disposal unit 205 and associated measurement devices 210 can be used to determine compliance with waste disposal regulation, which can occur automatically and/or with some level of manual activities being required of human agents.

For example, an electronic scale can be added to the disposal unit 205 to measure the weight of the waste being processed. Examples of other data measurements devices 210 (besides a scale) can include, but are not limited to, an air quality sensor, a manometer, a particle count sensor, a radiation sensor, an air volume sensor, and the like.

The data measurements devices 210 can communicate their readings with a data collection component 220 of a computing device 215. The computing device 215 can represent a variety of electronic components (user interfaces, etc.) configured to communicate with the disposal unit 205 and/or data measurements devices 210 and execute the commands of the data collection component 220.

In another contemplated embodiment, the computing device 215 can be implemented as an embedded computer that can be integrated within the disposal unit 205. In such an embodiment, the disposal unit 205 can be modified to include the necessary elements to allow connection to the network 260. In one embodiment, computing device 215 can be implemented modularly as a detachable component of disposal unit 205. In one embodiment, disposal unit 205 can be electronically docked to ports of a computing device 215, which permits peripheral devices (including data measurement device(s) 210), sensors, and other electronically coupled components communicate digitally encoded data. In one embodiment, the disposal unit 205 can have a docketing station to perform this electronic coupling. Components of unit 205 can be communicatively linked to device 215 through wired (e.g., peripheral ports, a communication bus, etc) or wireless (e.g., BLUETOOTH, ZIGBE, WIRELESS USB, WIFI, IR, etc.) connections.

The data collection component 220 can represent a computer program product (e.g., a software/firmware application or module that is stored on a tangible storage device) configured to aggregate the waste data 235 measured by the data measurements devices 210 for a specific lot of waste being processed by the disposal unit 205. Aggregation of the waste data 235 by the data collection component 220 can also include the execution of additional operations, such as the calculation of related indices or properties, unit of measure conversions, and data formatting. The data collection component 220 can be further configured to perform basic limit checking functions, such as determining if the collected air particles require additional processing for disposal or are unsafe for unprotected handling.

Once all the waste data 235 is collected, the data collection component 220 can send the waste data 235 to the data server 225 for storage in a data store 230. The data server 225 and a data store 230 can represent the hardware and/or software components necessary to manage the electronic storage of and access to the waste data 235. For example, the data server 225 and data store 230 can be existing elements of a hospital's network 260, with a specified data section set aside for the waste data 235. Although expressed as a tangible storage medium connected to device 215 via a network 260, the disclosure is not so limited. For example, in one embodiment, store 230 can be a tangible storage medium local to device 215, such as a removal media (e.g., a removable optical media, a flash memory, etc.).

It should be appreciated that conventional methods for collecting waste data 235 are manual in nature, exposing personnel to harmful conditions when taking the measurements. Further, manual inputting of the information permits transcription errors, lost data, and other such errors that diminish an accuracy of reported information. The automated collection of waste data 235, as shown in system 200, can further reduce such exposures as well as increase measurement accuracy.

In another embodiment, system 200 can be configured to function without the network 260 component. In such an embodiment, the computing device 215 and/or data collection component 220 can be configured to provide the collected waste data 235 to an intermediary device (not shown) that can be physically transported to the data server 225 and/or data store 230. In such an embodiment, security measurements (such as use of unique identification keys per disposal unit 205, encryption techniques, metering techniques, and data tracking technologies, etc.) can be utilized to ensure data obtained from component 220 is properly and securely conveyed to server 225.

For example, the data collection component 220 can store the waste data 235 on a removable memory storage device, like a universal serial bus (USB) memory stick, which a user 255 can then disconnect from the computing device 215. The user 255 can then take the USB memory stick to the physical location of the data server 225, connect the USB memory stick to the data server 225, and transfer the waste data 235 from the USB memory stick into the data store 230.

With the waste data 235 electronically stored in a network-accessible location, the performance of tasks requiring use of the waste data 235 can be improved. Examples of such task can include, but are not limited to, report generation, data analysis, historical trend analysis, inventory management, regulatory compliance, data validation, and the like.

The additional components shown in system 200 can further illustrate this impact upon task improvement. The data server 225 can be further configured to automatically and electronically report the collected waste data 235 to a designated reporting agency 240. Such a reporting process can reduce the role of a user 255 from manually collating the waste data 235 to simply verifying the waste data 235.

Even if not automatic, a user 255 can utilize a waste management/reporting application 250 running on a client device 245 to efficiently access/process the waste data 235. The waste management/reporting application 250 can represent a software program configured to communicate with the data server 225 to access the waste data 235. The waste management/reporting application 250 can further include a variety of data analysis and/or reporting functions to allow the user 255 to perform additional operations upon the waste data 235.

For example, a user 255 can use the waste management/reporting application 250 to automatically populate an electronic form to be submitted to a reporting agency 240. In one embodiment, the reporting can also be submitted via an email message. In other embodiments, reporting can occur via an alternative electronic communication, which can be a unidirectional or bidirectional communication. For example, a cloud based collaboration space can be established for reporting, as can a network space, or a Web based one (e.g., HTTP or HTTPS compatible). Additionally, the data collection component 220, software executing on the data server 225, and/or application 250 can convert and format data collected from one or more devices 215.

For example, in one embodiment, data collected by component 220 and placed in data store 230 can be gathered and used to automatically populate an EXCEL spreadsheet (or other spreadsheet format). The spreadsheet can have columns dictated at least in part by one or more reporting agencies 240. For example, columns can include the values shown in pickup instance table 232, such as building/room, date of pickup, manifest number, a date the manifest was received, the number of days for receipt of the returned manifest form, a Boolean value (e.g., Yes/No) for whether the manifest was received within 45 days, a quantity of waste in pounds, and a set of waste codes for the waste. The EXCEL spreadsheet can be saved, manipulated, and ultimately reported to agency 240 (or data can be pulled from it to populate a form used by a reporting agency 240).

Of course, use of EXCEL is simply one example used to express an ability to adapt the data gathered herein to a set of commonly available software applications. Other software applications can be used in other contemplated embodiments of the invention. For example, a relational database management system (RDBMS) including table 232 (or attributes shown in table 232) can be used in another embodiment of the invention. Data of the data store 230 can be synchronized and/or otherwise conveyed to databases of the reporting agency 240.

Any number of optional safeguards can be implemented to ensure data accuracy and lack of manipulation occurrences. For example, in one embodiment, a data reporting agency, such as the EPA, can require data be stored in an encrypted and proprietary form, while in data store 230, which is automatically reported to agency 240. Use of an encrypted or proprietary form of data can minimize instances of tampering with the raw data. In another example, digital certificates, hidden metadata, and/or measures can be implemented to ensure the data received by the agency 240 is accurate. This represents an improvement over current practices, which are manual in nature and subject to recordation inaccuracies, transcription errors, and intentional manipulations.

In one embodiment, alerts and reporting functions can be included in system 200 to enhance safety while disposing of hazardous material. For example, one or more data measurement devices 210 can be used to sense leakages of unit 205. When a leakage is detected, an appropriate maintenance person and other appropriate personnel can be alerted via an automated text message, telephone call, fax, or other messaging technique. Further, on unit 205 alerting (such as through LED display panels, an audible warning, a problem indicating flashing light, etc.) can be implemented to ensure suitable personnel are alerted when actions related to the disposal unit 205 need to be taken. These actions can include alerts for emptying the unit 205 when full, alerts for detection of leakage that releases harmful vapors from unit 205, and the like.

Network 260 can include any hardware/software/and firmware necessary to convey data encoded within carrier waves. Data can be contained within analog or digital signals and conveyed though data or voice channels. Network 260 can include local components and data pathways necessary for communications to be exchanged among computing device components and between integrated device components and peripheral devices. Network 260 can also include network equipment, such as routers, data lines, hubs, and intermediary servers which together form a data network, such as the Internet. Network 260 can also include circuit-based communication components and mobile communication components, such as telephony switches, modems, cellular communication towers, and the like. Network 260 can include line based and/or wireless communication pathways.

As used herein, presented data store 230 can be a physical or virtual storage space configured to store digital information. Data store 230 can be physically implemented within any type of hardware including, but not limited to, a magnetic disk, an optical disk, a semiconductor memory, a digitally encoded plastic memory, a holographic memory, or any other recording medium. Data store 230 can be a stand-alone storage unit as well as a storage unit formed from a plurality of physical devices. Additionally, information can be stored within data store 230 in a variety of manners. For example, information can be stored within a database structure or can be stored within one or more files of a file storage system, where each file may or may not be indexed for information searching purposes. Further, data store 230 can utilize one or more encryption mechanisms to protect stored information from unauthorized access.

FIG. 2 is a schematic diagram of a waste disposal system 200 for safely disposing hazardous material in accordance with an embodiment of the inventive arrangements disclosed herein. As shown, waste 210 can be placed within a disposal unit 215 through an insertion component 220.

The disposal unit 215 can be a substantially closed system, designed to permit complete waste 210 containment. For example, when the waste 210 can include airborne particles, the unit 215 can be a closed, air-tight system designed to prevent an escape of airborne particles. The insertion component 220 can ensure the waste 210 is sealed once placed in unit 215 to prevent external leakages and exposure. Disposal unit 215 can be implemented as any of a variety of different disposal containers 222, each able to contain waste 210, which can be sealed by the container sealant mechanism 224 to prevent the waste 210 from escaping once contained. For example, the containers 222 can include bags, hardened plastic baskets, chemo bins, and the like. Waste disposed of in the containers 222 (which is prevented from escaping) can include vapors, radiation, and small particles.

The container sealant mechanism 224 can represent one or more mechanisms for sealing the disposal container 222. Contemplated examples of the container sealant mechanism 224 can include, but are not limited to, one or more manual manipulators, an automated vacuum-sealing component, an automated heat-sealing component, use of an adhesive to seal container 222, and the like. The seal established by the container sealant mechanism 224 can be an air tight one.

Once the disposal container 222 is sealed, an air extraction unit 228 can remove airborne particles or other potentially dangerous trace elements from the disposal unit 215. The removed air can be placed within an air container 226. In one embodiment, the air container 226 can be a separate container from disposal container 222. In another implementation, the disposal container 222 can be an air tight container that also functions as the air container 226. In still another implementation, the air container 226 can be a separately sealed container included inside the disposal container 222. Of course, using the disposal container 222 to contain air can alter an order in which the disposal container 222 is sealed relative to when the disposal unit 215 extracts the air.

After air collection and the sealing of the disposal container 222, the air collected in the air container 226 can be treated by an air sanitation component 230. The air sanitation component 230 can include one or more air treatment mechanisms configured to improve the air quality of the collected air to a predetermined/acceptable level.

Examples of air treatment mechanisms that can be utilized in the air sanitation component 230 can include, but are not limited to, a heat sterilization mechanism, an incineration mechanism, an ultraviolet (UV) disinfection mechanism, a filtration mechanism, a photo-catalytic sanitation mechanism, an oxidation mechanism, an ionization mechanism, and the like. For example, the air within the air container 226 can be exposed to a UV disinfection wand before passing through an active carbon filter. Any number (0 . . . N) of different sanitation components 230 can be cooperatively utilized.

Embodiments are contemplated, where air treatment resulting from use of one or more components 230 is sufficient to permit sanitized air to be conveyed from disposal unit 215 to an external environment, as opposed to requiring it be stored in air container 226. Further, embodiments are contemplated where sensors are used to examine air inside the unit 215, where different steps are taken based upon sensor results. For example, results can indicate that interior air of unit 215 should be cycled (0 . . . N times) through one or more of the sanitation components and then ejected into an exterior environment (by air extraction unit 228). Different results can indicate that interior air of unit 215 should be captured in air container 226, then further sanitation actions (using components 230 and/or cleaning component(s) 234) should be taken to additionally cleanse unit 215 of harmful vapors/residue.

Once the collected air has been sanitized to the predetermined level, an air exhaust element 232 can be used to expel the sanitized air 255 from the disposal unit 215. The air exhaust element 232 can be configured to optionally expel the sanitized air 255 into the immediate environment of the disposal unit 215. Alternately, the air exhaust element 232 can be connected to a ventilation system (not shown) external to the disposal unit 215.

The disposal unit 215 can optionally include an additional cleansing component 234, such as a component that sprays a sanitizing liquid into the interior of disposal unit 215 to ensure the disposal unit 215 is free of waste 210. Disposal unit 215 can also include one or more optional environment sensors 236 designed to detect when the disposal unit 215 is free from harmful waste 210 (which includes vapors). The environment sensor 236 can be linked to a removal component 240 so that the removal component 240 is unable to be opened until the interior environment of the disposal unit 215 is safe.

An optional safety indicator 238 can provide an indicator as to conditions determined by the one or more environment sensors 236. For example, the safety indicator 238 can display text concerning radiation levels, airborne pathogen levels, and other important metrics concerning the interior condition of the disposal unit 215. In another example, the safety indicator 238 can be implemented as a light providing a warning when it is safe/unsafe to open the disposal unit 215. The removal component 240 can be a component through which the sealed waste 245 and/or removed air/particles 250 are able to be safely removed.

Figure 3:
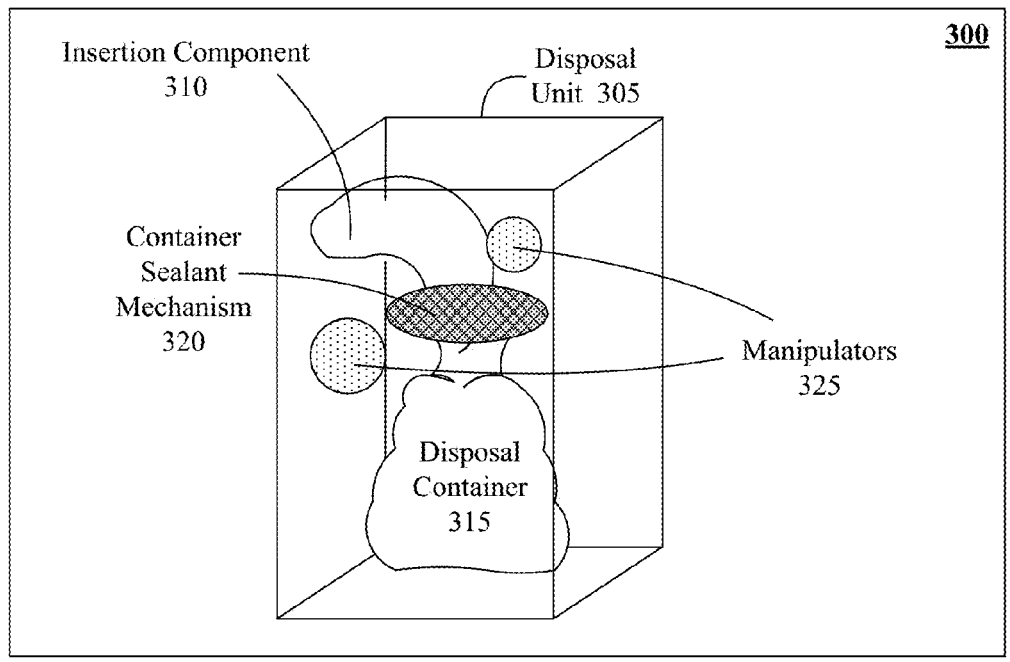
FIG. 3 is a schematic diagram of a specific implementation instance of a disposal unit that emphasizes the incorporation of a container sealant mechanism.
Figure 3:
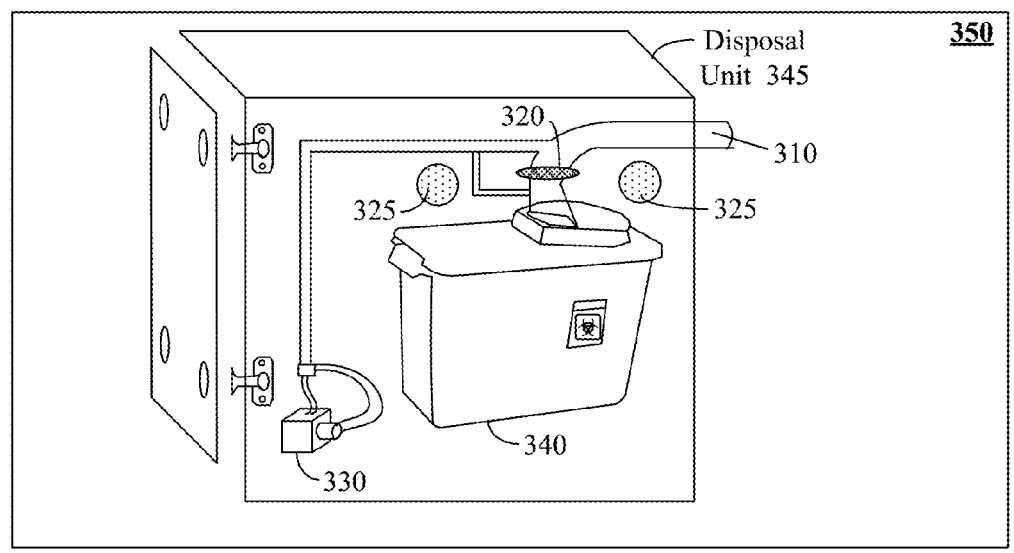

FIG. 3 shows a schematic diagram of a specific implementation instance 300, 350 of a disposal unit 305 that has the incorporation of a container sealant mechanism 320. Implementation instance 300, 350 can be utilized within the context of systems 200 and 200, and/or the embodiments of the disposal unit 305, 345 described within U.S. patent application Ser. No. 11/946,283. The disposal unit 305 of implementation instance 300 can be configured to utilize a container sealant mechanism 320 in addition to manipulators 325.

It is important to emphasis that in implementation instance 300, the container sealant mechanism 320 is used to seal the disposal container 315, not the manipulators 325. That is, an operator of the disposal unit 305 is not required to seal the disposal container 315 using the manipulators 325 (i.e., the operator need not use the manipulators 325 to apply a twist tie to a plastic bag 315).

The insertion component 310 for receiving waste can be terminally connected to the container sealant mechanism 320, which can be connected to the disposal container 315, such as a sealable plastic bag. The manipulators 325 can be used to connect the disposal container 315 to the container sealant mechanism 320 and/or operate the container sealant mechanism 320. Alternately, the container sealant mechanism 320 can be configured to execute automatically, triggered by the disposal unit 305. Any number of configurable conditions can trigger the automatic execution of sealant mechanism 320, such as the weight of the disposal container 315, an expiration of a maximum time that hazardous material has been left in container 315, a sensor reading indicating that a previously defined toxicity level has been reached, and other such conditions or combinations thereof.

A variety of container sealant mechanisms 320 can be contemplated for this implementation instance 300. In one such contemplation, the container sealant mechanism 320 can include the components to vacuum seal the disposal container 315. In another embodiment, the container sealant mechanism 320 can include parallel heating elements that collapse and melt the opening of the disposal container 315. In one embodiment, a top potion of container 315 can have a self-sealing strip, which seals the container 315 when pressed to an opposing potion of container 315 by mechanism 320. In one embodiment, an adhesive can be ejected by mechanism 320, which seals container 315.

It should be noted that the contemplated container sealant mechanisms 320 for implementation instance 300 are discussed in regards to the use of a plastic bag as the disposal container 315. However, these contemplations can be expanded to accommodate other types of disposal containers 315.

Embodiment 350 shows one such example where container 340 is incorporated within the disposal unit 345. Container 340 can be a standardized container, such as an FDA approved biohazard collection box, a sharps box for needle disposal, and the like. These types of containers are often present in doctor's offices and hospitals. These standard containers 340 are typically environmentally exposed, which causes air from the containers 340 to disseminate into the local environment. In many instances, this can result in bystanders/patients/doctors/nurses being exposed to harmful vapors, particles, and other substances. In embodiment 350, an insertion component 310 is attached to the container 340, which itself is sealed. Air can be extracted from the container, using a pump 330, where it can be optionally filtered, incinerated, or contained. Unit 345 inhibits outgoing air from container 340 from being disseminated into the local environment (one external to unit 345). When container 340 is full, manipulators 325 can be used to seal the container 340 for extraction. Alternatively, container sealant mechanism 320 can be used to seal container 340 for disposal. Container 340 can then be safely removed from unit 345 and handled properly. Components of embodiment 350 are illustrative only, and can include any of the variations of components described herein and/or described in U.S. patent application Ser. No. 11/946,283. It should be appreciated adapting unit 345 to work with existing containers 340 can minimize inventory, implementation cost, established contracts, and can ensure current disposal processes are minimally affected, while nevertheless realizing positive environmental benefits described herein.

Figure 4:
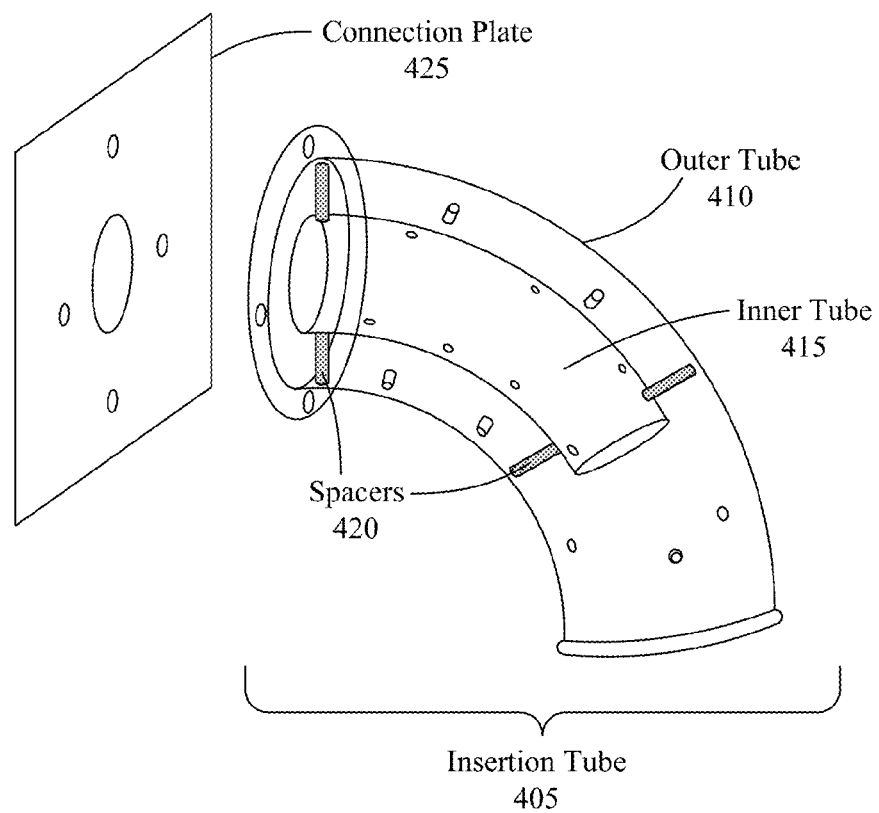
FIG. 4 illustrates a specific implementation instance of an insertion tube for the disposal unit.

FIG. 4 illustrates a specific implementation instance 400 of an insertion tube 405 for the disposal unit. Implementation instance 400 can be utilized within the context of systems 100 and 200, implementation instance 300, and/or the embodiments of the disposal unit described within U.S. patent application Ser. No. 11/946,283.

In implementation instance 400, the insertion tube 405 can be connected to a connection plate 425 within the interior of the disposal unit. The insertion tube 405 can be comprised of an outer tube 410 and an inner tube 415 that can be separated by spacers 420. Thus, both the outer tube 410 and inner tube 415 can be adjusted simultaneously by the same movement.

It should be appreciated that the insertion tube 405 shown in implementation instance 400 can allow for a variety of configurations that can be used to tailor and/or enhance the performance of the disposal unit. The following are examples highlighting these enhancement capabilities.

The outer tube 410 can be made from a material having qualities that are different and/or specific from the material that the inner tube 415 is made from. Such a configuration can be useful when the disposal unit is required to handle waste containing radioactive byproducts or ferrous metals. For example, an inner tube 415 made of a material that is magnetically inert can better ensure that ferrous metal waste does not aggregate in the insertion tube 405.

Additionally, varied configurations of materials comprising the inner tube 415 and the outer tube 410 can expand the range of waste that the disposal unit is able to process. That is, an insertion tube 405 configuration can be switched to a different configuration in order to handle a different type of waste and/or waste byproducts.

Another advantage of a dual-tube insertion tube 405 can be part longevity. For example, the insertion tube 405 can continue to function despite the presence of a defect (i.e., tear, hole, etc.) in either the inner tube 415 or the outer tube 410. That is, the outer tube 410 can be thought of as a redundant inner tube 415, allowing the disposal unit to continue functioning as long as the integrity of both tubes 410 and 415 has not been compromised.

The spacers 420 separating the inner 415 and outer tubes 410 can also be of various materials, allowing another level of insertion tube 405 customization. For example, the spacers 420 can be of a flexible material to allow for the insertion tube 405 to be moved without stressing the spacers' 420 connection points with the outer tube 410 and/or inner tube 415. This can be especially useful should the interior chamber of the disposal unit be put under the effect of a vacuum. Additionally, the quantity of spacers 420 used can be varied to handle more or less stress. In one embodiment, inhibitors can be inserted into the inner tube 415 (and/or the outer tube 415) to ensure a unidirectional flow of material (e.g., prevent backflow).

It should be noted that the configurations discussed above and presented in implementation instance 400 focus on the use of two tubes. An embodiment of the present invention is not limited as such, and can be expanded to apply to an insertion tube 405 comprising of more than two tubes. As such, the various layers of tubes can be configured to further act as a filtration mechanism for the disposal unit.

Figure 5:
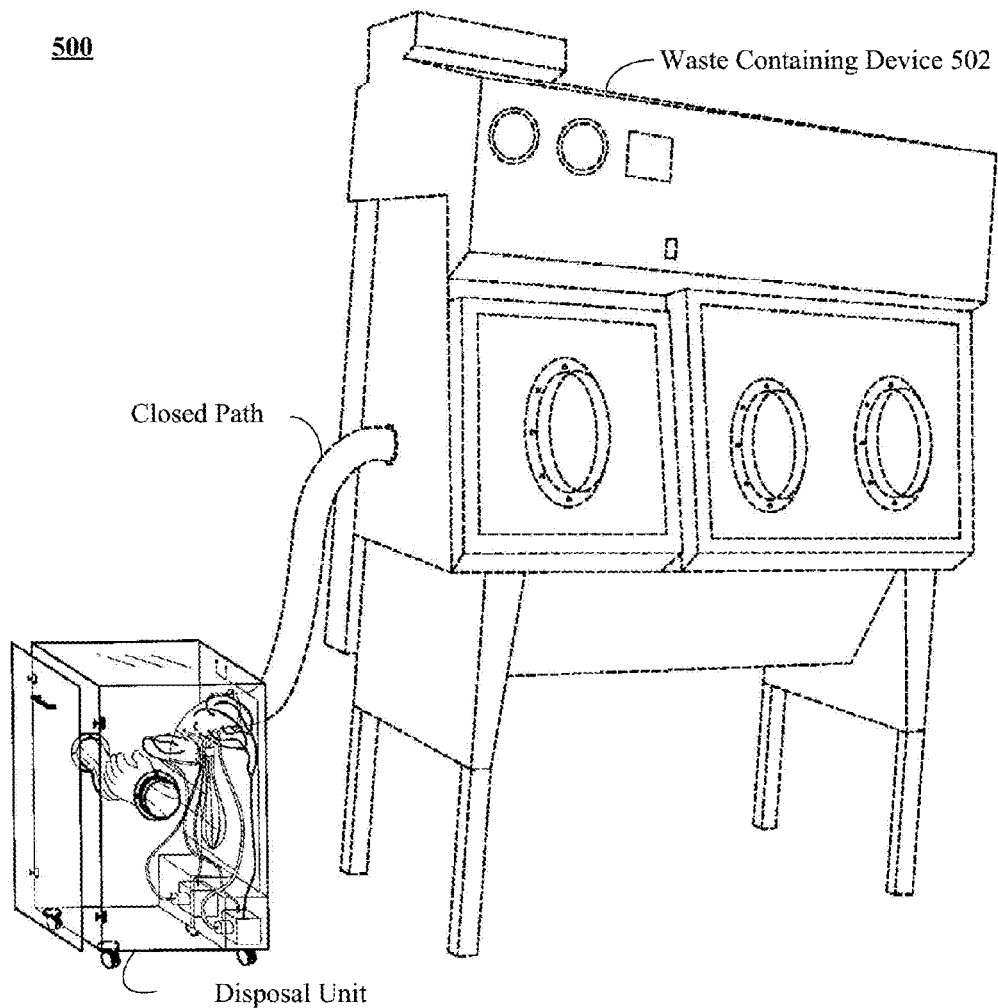
FIG. 5 shows a system that includes a waste containing device, which is connected to the disposal unit via a closed path in accordance with an embodiment.

FIG. 5 shows a system 500 that includes a waste containing device 502, which is connected to the disposal unit 520 via a closed path 504 in accordance with an embodiment. Specifically, the device 502 can be a chemical fume hood. A pre-existing, commercial-off-the shelf chemical hood can be adapted to include disposal unit 520. For example, instead of permitting the air/particles contained within a hood (device 502) to be ejected to an environment after an optional filtering step, the emissions can be conveyed along the closed path 504, to the unit 520. The unit 520 can process hood (202) emissions and safely discard them.

In one embodiment, an auto-cleaning feature can be used to rinse/sweep chemicals from device 502, along the path 504, where they are safely discarded/handled by unit 520. The unit 520 can optionally include a one-way aperture, where users of device 502 can also discard waste. In a different implementation, the disposal unit 520 and/or disposal features of unit 520 can be integrated into device 502 to create a single, integrated device, through which chemicals and other byproducts can be safely discarded.

Figure 6:
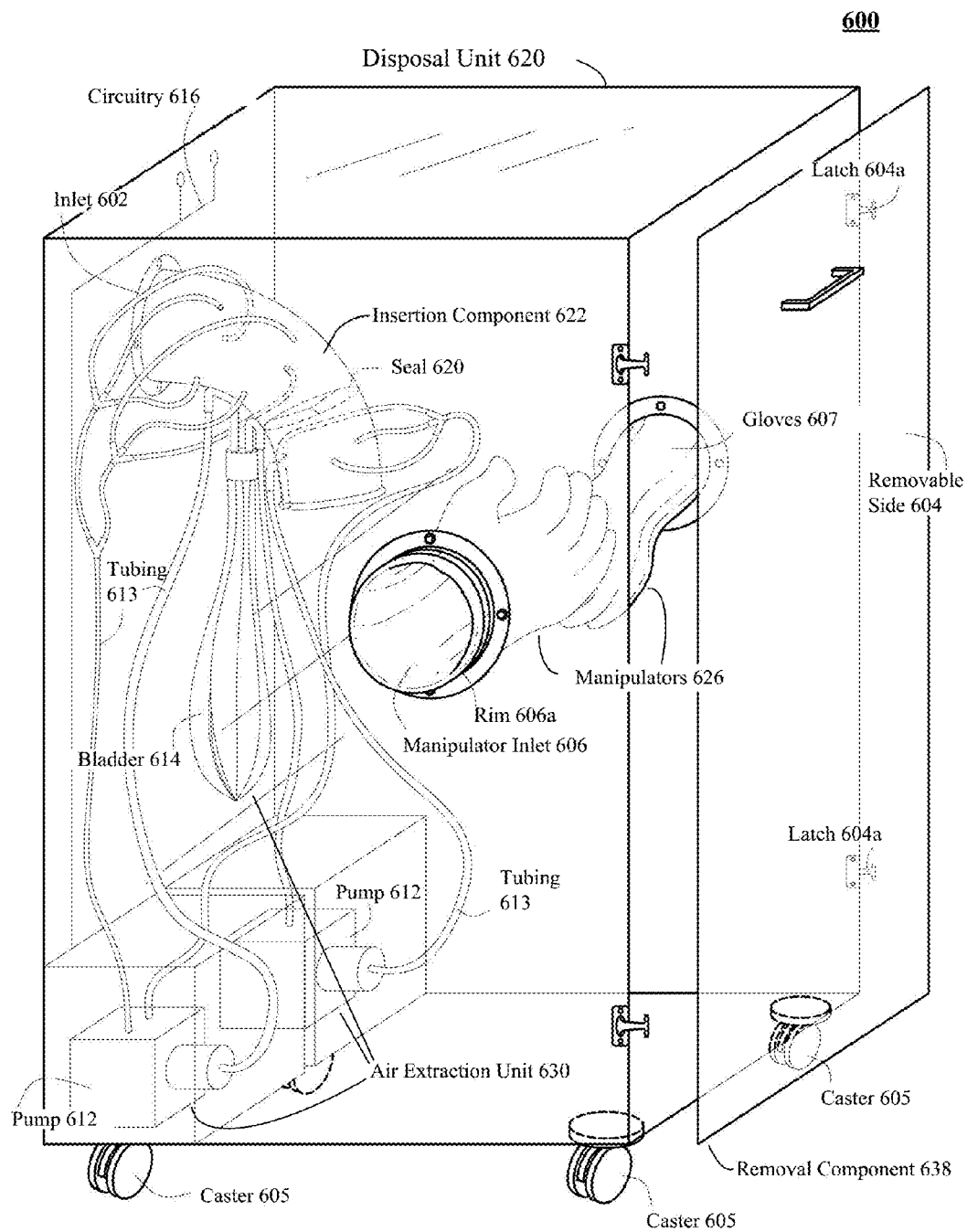
FIG. 6 is a schematic diagram of a specific instance of a disposal unit in accordance with an embodiment.

FIG. 6 is a schematic diagram of a specific instance 600 of a disposal unit 620 in accordance with an embodiment. In implementation instance 600, an inlet 602 can be part of an insertion component 622 for receiving waste, which can be terminally connected to a disposal container, such as a sealable trash bag. Manipulators 626 can be used to position the disposal container about the insertion component. The insertion component 622 can include a one-way seal 620 to help contain inserted waste and to ensure harmful byproducts from inserted waste are not discharged.

Air extraction unit 630 can consist of one or more pumps 612 connected to the insertion component 622 via tubing 613. An air bladder 614 can inflate to pull air from an environment of unit 620. Once full, and once an air-tight disposal container (e.g., bag) is connected to the insertion component 622, the bladder 614 can release captured air/particles into the disposal container (or other container, such as a separate air containment unit/air reclamation component). After the air is injected into the disposal container, it can be sealed via the manipulators 626, which in one embodiment can be a set of rubberized gloves 607. Once sealed, the removable side 604 can be detached to permit the now sealed disposal container to be removed.

As illustrated in instance 600, the surfaces of contact between the side 604 and the perimeter of the unit 620 can be covered along the curves by a foamy or other sealing material (omitted in the drawings) that ensures air tight sealing while the environment of unit 620 is closed.

In one of the embodiment a bottom of the unit 620 can include a set of casters 605 annealed or secured on each corner allowing the end user to roll the unit 620 around as needed. Perpendicular to the surface with the castors 605, can be a surface that has four latches. Two latches 604a can be positioned on one side of the unit 620 and the other two latches 604a are on the opposite side. During normal operations these latches 604a can be pulled back. When the operator is required to remove the side 604 completely and remove the said solid waste bag, the latches 604a can be released forward.

Further illustratively in one of the embodiments of the claimed invention the inlet 602 can be a downward arc shaped tube. Two of the sides of the unit 620 can have an opening inlet featuring a rim 606a, preferably a steel rim, affixed to said waste collection bin with a lip shaped in a way to allow rubber gloves 607 to be inserted inside and around the inside of the cylindrical lip of the unit 620. These gloves 607 can be manipulators 626 that permit an operator to insert their hands and tie a bag containing said solid waste without coming into contact of the inside of the unit 620, which remains in a closed state while the gloves 607 are utilized.

A vacuum can be generated by a vacuum pump 612 connected to a plurality of non-collapsible vacuum quality tubing 613 that in turn supports a low pressure environment inside the possibly metallic cylindrical tube. Inherent in the tubing 613 can be check valves (omitted in the drawings), which prevent air from seeping back to its original origin. The outlet of the vacuum pump 612 can be connected to an air bladder 614 where the air sucked in by the pump 612 is ultimately collected.

The vacuum pump 612 can be installed on the inside of the disposal unit 620 located at the bottom in one corner of the floor of the unit 620, although exterior mounting of the pumps 612 and other positions are also possible. Each pump 612 can be connected to a power source, such as an 115v, 230v, or DC source. A contemplated range of delivery for the pump 612 in one embodiment can be between 0.5 Liter/min to 20 Liter/min.

Pressure of the air in the bladder 614 can be monitored by a pressure gauge, such that in one of the illustrative embodiments of the claimed invention lights or other warning indicators can alert users when the air lines 613 or air bladder 614 become compromised (when pressure is unexpectedly lost).

As shown in instance 600, the air bladder 614 can be attached to the bottom portion of the metallic cylinder tube, approximately equidistant between both openings. The air bladder 614 can be connected with the solid waste bin by a vacuum quality non-collapsible tubing system 613. Controls of the unit 620 can regulate a gas flow between the air bladder 614 and the solid waste disposal bag. When a user selectable control is pressed, the vacuum system can be redirected by the means of a plurality of tubes 613, valves, switches, and connections, so that the air flow is directed from the air bladder 614 to the waste bag.

A function of the air bladder 614 can be to capture any noxious gas originated by the waste introduced through the initial aperture 602 and to hold the waste/particles/airborne pathogens until the possibly tainted air can be redirected to the waste bag, which is then finally removed and incinerated. Instance 600 is novel over conventional systems as it is a closed system where vapors, gases, dust, odors, airborne pathogens, and the like are temporarily stored and re-directed to the waste bin without exposing the exterior environment or a waste handler. Sealed waste can be handled safely in accordance with any applicable guidelines, such as Federal Guidelines for incinerating chemotherapy resulting waste.

It should be appreciated that a specific application of instance 600 for healthcare professionals in a hospital or an out-patient clinic, engaging in chemotherapy or other wastes can be profound. There is currently no appropriate protection when disposing of chemotherapy contaminated waste in bins that are not sealed or lids that remain ajar. As a result, noxious and volatile gases can seep out in to the surrounding environment and render the health care professional compromised and subject to various health concerns. The main function of the air bladder 614 is to act as a staging area to hold contaminated air and store it until the chemotherapy waste bag is ready to be changed, at which time the air bladder 614 can be evacuated into the chemotherapy waste bag by selecting a user accessible control.

Figure 7:
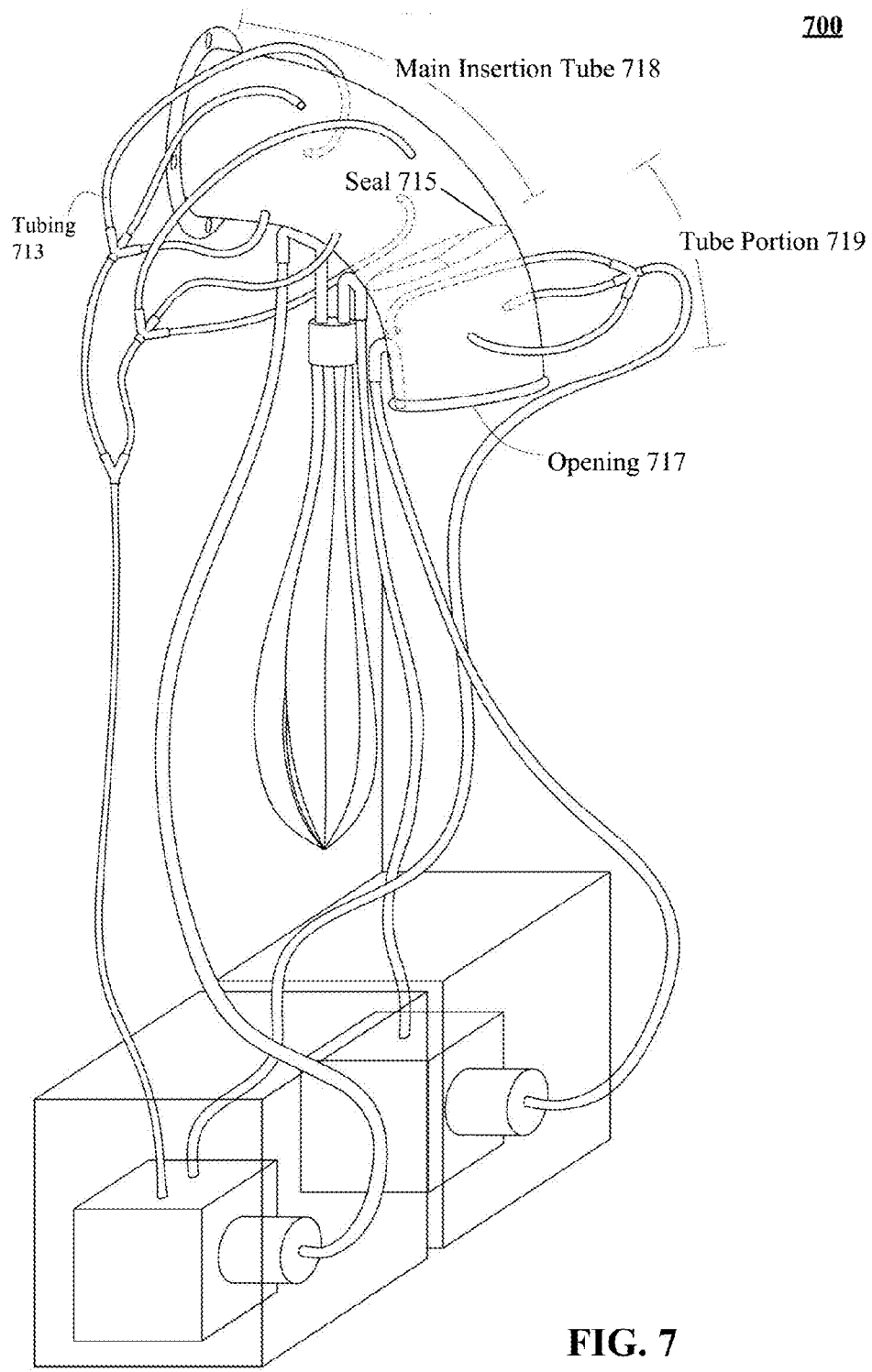
FIG. 7 provides a detailed view of the closed vacuum system of the disposal unit in accordance with one embodiment.

FIG. 7 provides a detailed view 700 of the closed vacuum system of the disposal unit in accordance with one embodiment. Specifically, view 700 shows the tubing 713, which is connected to the main insertion tube 718 and the bladder. Tube portions 719 can be positioned on both sides of a seal 715 contained within the insertion tube 718 to help direct air flow. The opening 717 can be sealed to a disposal container, such as a sealable, air-tight waste bag.

Figure 8:
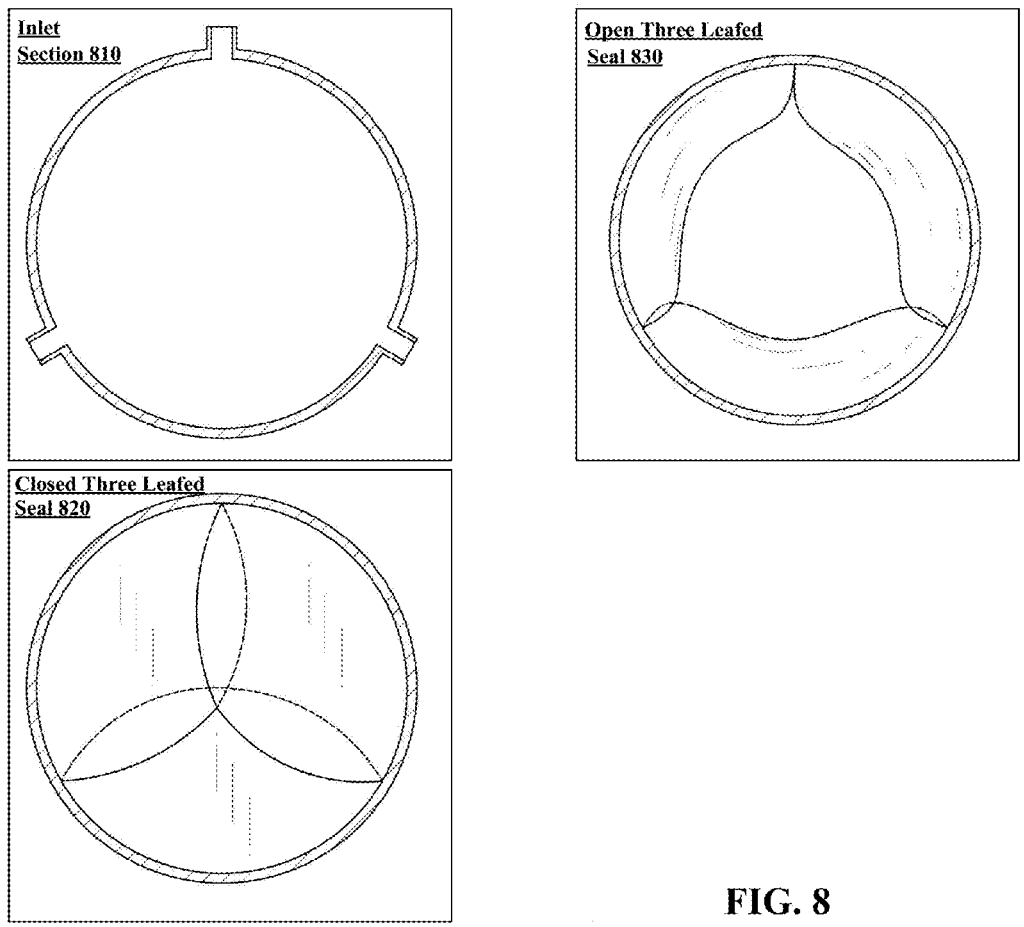
FIG. 8 shows a cross sectional view of an insertion tube of the disposal unit in accordance with an embodiment of the disclosure.

FIG. 8 shows a cross sectional view 810 of an insertion tube of the disposal unit in accordance with an embodiment of the disclosure. Views for a closed seal 820 and an open seal 830 are shown. The represented seal 820, 830 can be the seal 715 contained within an insertion tube of the disposal unit.

Figure 9:
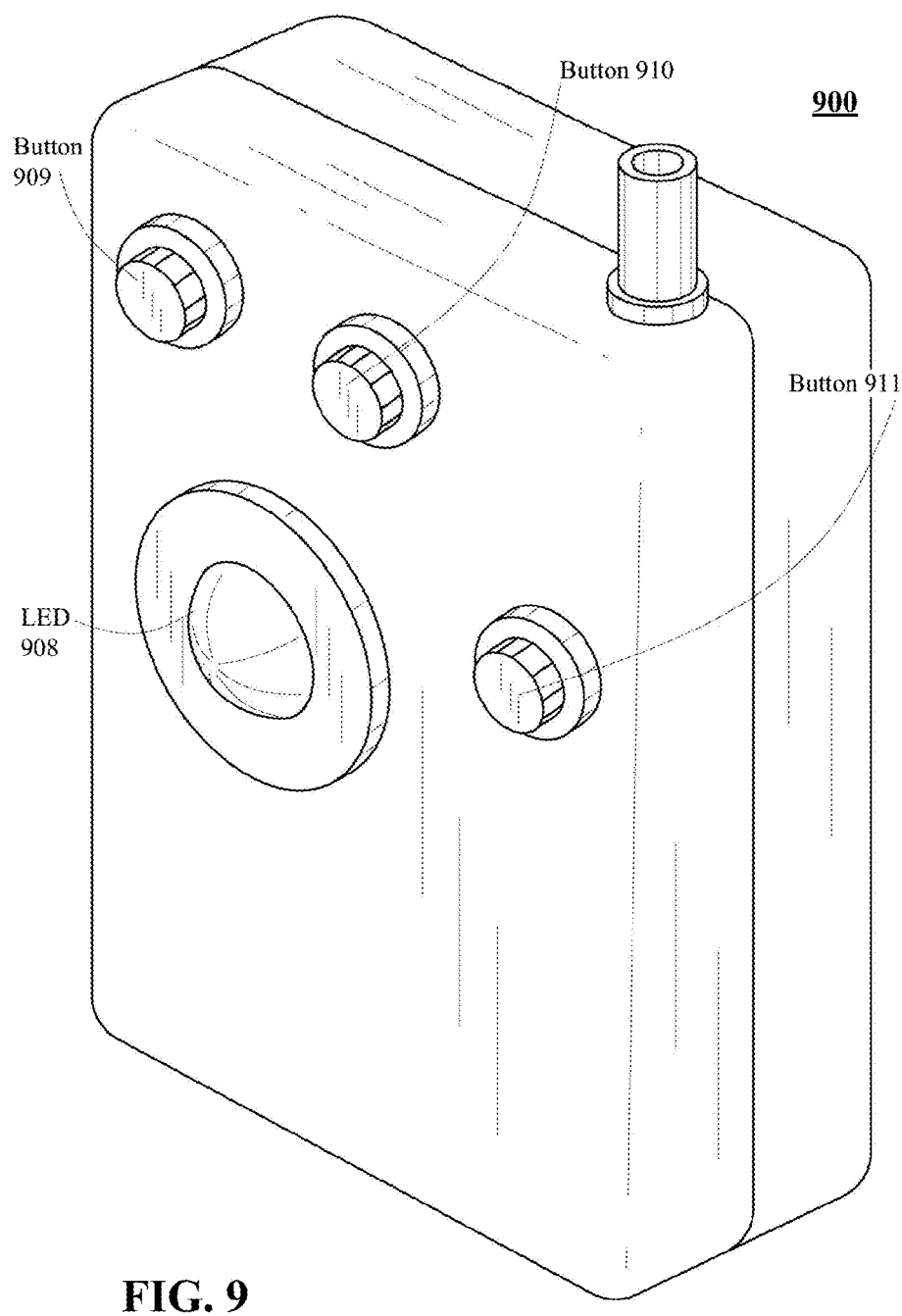
FIG. 9 illustrates a control unit for a disposal unit in accordance with an embodiment of the disclosure.

FIG. 9 illustrates a control unit 900 for a disposal unit in accordance with an embodiment of the disclosure. The control unit can include a set of user selectable controls, such as buttons 909, 910, and 911. Button 909 can cause air within a disposal unit to be temporarily contained (e.g., can inflate a bladder or actuate a similar component). Button 910 can cause temporarily captured air (e.g., air within an inflated bladder) to be conveyed into a disposal container (e.g., a sealable, airtight, trash bag). Button 911 can capture any escaped air, once a disposal bag has been sealed and before an operator opens the previously closed system of the waste disposal unit. LED indicator 908 can represent a warning light, which can indicate various system concerns, such as a presence of harmful substances within an environment of the disposal unit, a potential leakage in the air system of the disposal unit, and the like.

The present invention may be realized in hardware, software or a combination of hardware and software. The present invention may be realized in a centralized fashion in one computer system or in a distributed fashion where different elements are spread across several interconnected computer systems. Any kind of computer system or other apparatus adapted for carrying out methods described herein is suited. A typical combination of hardware and software may be a general purpose computer system with a computer program that, when being loaded and executed, controls the computer system such that it carries out the methods described herein.

The present invention also may be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

What is claimed is:

1. A disposal unit comprising:
   a substantially air tight chamber;
   an insertion component for inserting waste into the chamber, wherein the insertion component comprises an insertion tube and a one-way seal, and wherein said insertion tube comprises an inner tube and an outer tube, wherein a plurality of spacers separate the outer tube from the inner tube;
   a disposal container for removing the inserted waste from the disposal unit;
   a container sealant mechanism configured to allow a sealing of the disposal container; and
   an air extraction unit configured to capture air or airborne particles from the substantially air tight chamber to minimize exposure to the air or the airborne particles from the inserted waste, wherein the exposure to the air or airborne particles is minimized to humans placing the waste into the insertion component, to humans removing the disposal container from the disposal unit, or to humans proximate to the disposal unit.

2. The disposal unit of claim 1, further comprising:
   an air sanitation component configured to sanitize the captured air or airborne particles to a predetermined air quality level, wherein harmful airborne byproducts of the inserted waste are reduced or neutralized by the air sanitation component.

3. The disposal unit of claim 2, wherein the air sanitation component utilizes at least one of heat sterilization, incineration, ultraviolet (UV) disinfection, filtration, photo-catalytic sanitation, oxidation, and ionization.

4. The disposal unit of claim 2, wherein the air sanitation component further comprises:
   an exhaust element configured to dissipate the sanitized air from the disposal unit.

5. The disposal unit of claim 1, wherein the container sealant mechanism comprises a manipulator, an automated vacuum-sealing component, an automated heat-sealing component, or combinations thereof.

6. The disposal unit of claim 5, wherein the container sealant mechanism is the manipulator, wherein the manipulator comprises a sealed glove through which a user of the disposal unit is able to insert his/her hands to seal the disposal container.

7. The disposal unit of claim 1, further comprising:
   at least one environmental sensor configured to detect whether an interior of the disposal unit contains harmful airborne byproducts of inserted waste.

8. The disposal unit of claim 7, further comprising:
   at least one safety indictor configured to notify a user of the disposal unit when a quantity of one or more byproducts detected by the at least one environmental sensor exceeds a previously established threshold.

9. The disposal unit of claim 1, further comprising:
   a removal component configured to have at least an open state and a closed state, wherein when in the closed state the substantially air tight chamber is approximately air tight, and wherein when in an open state, the substantially air tight chamber is not air tight, wherein when the removal component is in the open state, a disposal container included in the disposal unit is able to be removed.

10. A disposal unit comprising:
    a substantially air tight chamber;
    an insertion component for inserting waste into the chamber, wherein the insertion component comprises an insertion tube and a one-way seal, and wherein said insertion tube comprises an inner tube and an outer tube, wherein a plurality of spacers separate the outer tube from the inner tube;
    a disposal container for removing the inserted waste from the disposal unit;
    an air extraction unit configured to capture air or airborne particles from the substantially air tight chamber to minimize exposure to the air or the airborne particles; and;
    an air sanitation component configured to sanitize the captured air or airborne particles to a predetermined air quality level.

11. The disposal unit of claim 10, further comprising:
    a container sealant mechanism configured to allow a sealing of the disposal container, wherein once sealed by the container sealant mechanism, the disposal container containing the inserted waste is substantially air tight.

12. The disposal unit of claim 11, wherein the air sanitation component sanitizes the captured air or airborne particles after the disposal container is sealed by the container sealant mechanism, wherein the disposal unit further comprises:
    a door through which the disposal container is extracted, wherein the door is locked until the disposal container is sealed and air or airborne particles of the substantially air tight container is sanitized by the air sanitation component.

13. The disposal unit of claim 10, further comprising:
    an exhaust element configured to dissipate the sanitized air from the disposal unit.

14. The disposal unit of claim 10, wherein the air sanitation component utilizes heat sterilization.

15. The disposal unit of claim 10, wherein the air sanitation component utilizes incineration.

16. The disposal unit of claim 10, wherein the air sanitation component utilizes ultraviolet (UV) disinfection.

17. The disposal unit of claim 10, wherein the air sanitation component utilizes photo-catalytic sanitation, oxidation, ionization, or a combination thereof.

18. A disposal unit comprising:
    a substantially air tight chamber;
    an insertion component for inserting waste into the chamber, wherein the insertion component comprises an insertion tube and a one-way seal, and wherein said insertion tube comprises an inner tube and an outer tube, wherein a plurality of spacers separate the outer tube from the inner tube;
    a disposal container for removing the inserted waste from the disposal unit;
    a container sealant mechanism configured to allow a sealing of the disposal container;
    an air extraction unit configured to capture air or airborne particles from the substantially air tight chamber;
    at least one environmental sensor configured to detect whether an interior of the disposal unit contains harmful airborne byproducts of inserted waste; and
    at least one safety indictor configured to notify a user of the disposal unit when a quantity of one or more byproducts detected by the at least one environmental sensor exceeds a previously established threshold.

19. The disposal unit of claim 18, further comprising:
a closed vacuum system inside the air tight chamber, which is connected to the air extraction unit and to the insertion component.

\* \* \* \* \*